United States Patent
Fronda et al.

[11] Patent Number: 5,897,581
[45] Date of Patent: Apr. 27, 1999

[54] HEADWEAR FOR USE IN APPLYING COLD TO A PERSON'S SCALP

[75] Inventors: Carl Frank Fronda; Darren Lee Fronda; Frank Derek Fronda, all of Beckenham, United Kingdom

[73] Assignee: Carl, Darren and Claire Fronda, United Kingdom

[21] Appl. No.: 08/793,637

[22] PCT Filed: Aug. 30, 1995

[86] PCT No.: PCT/GB95/02042

§ 371 Date: Feb. 27, 1997

§ 102(e) Date: Feb. 27, 1997

[87] PCT Pub. No.: WO96/06580

PCT Pub. Date: Mar. 7, 1996

[30] Foreign Application Priority Data

Aug. 31, 1994 [GB] United Kingdom .................. 9417691

[51] Int. Cl.[6] ...................................... A61F 7/00
[52] U.S. Cl. .................. 607/109; 607/112; 607/114
[58] Field of Search .................... 607/104, 108–112, 607/114; 165/46

[56] References Cited

U.S. PATENT DOCUMENTS

| 4,002,175 | 1/1977 | Brainard et al. | 607/109 |
| 4,138,743 | 2/1979 | Elkins et al. | |
| 4,805,620 | 2/1989 | Meistrell | 607/108 X |
| 4,854,319 | 8/1989 | Tobin | 607/109 |
| 4,891,501 | 1/1990 | Lipton | 607/109 X |
| 4,915,108 | 4/1990 | Sun | |
| 5,119,812 | 6/1992 | Angelo | 607/109 |

FOREIGN PATENT DOCUMENTS

| 0 449 299 A1 | 3/1991 | European Pat. Off. |
| 32 10 178 A1 | 3/1982 | Germany |
| 2130489 | 3/1983 | United Kingdom |
| 2 160 425 | 6/1984 | United Kingdom |

Primary Examiner—Brian L. Casler
Assistant Examiner—Ryan Carter
Attorney, Agent, or Firm—Iandiorio & Teska

[57] ABSTRACT

Headwear (2) for use in applying cold to a person's scalp, which headwear (2) is flat when it is not being worn, is foldable around a person's head (4) when it is being worn, and is securable on the person's head (4), by a plurality of fastener means (6), the headwear (2) being such that the folding nature of the headwear (2) and the plurality of fastener means (6) enables the headwear (2) to be folded as a close fit on the person's head (4) irrespective of different persons with different shapes and sizes of head, and the headwear (2) being such that is has double skinned portions (8, 10) which contain a cold retaining medium which gives up its cold to the person's scalp when the headwear (2) is being worn.

9 Claims, 5 Drawing Sheets

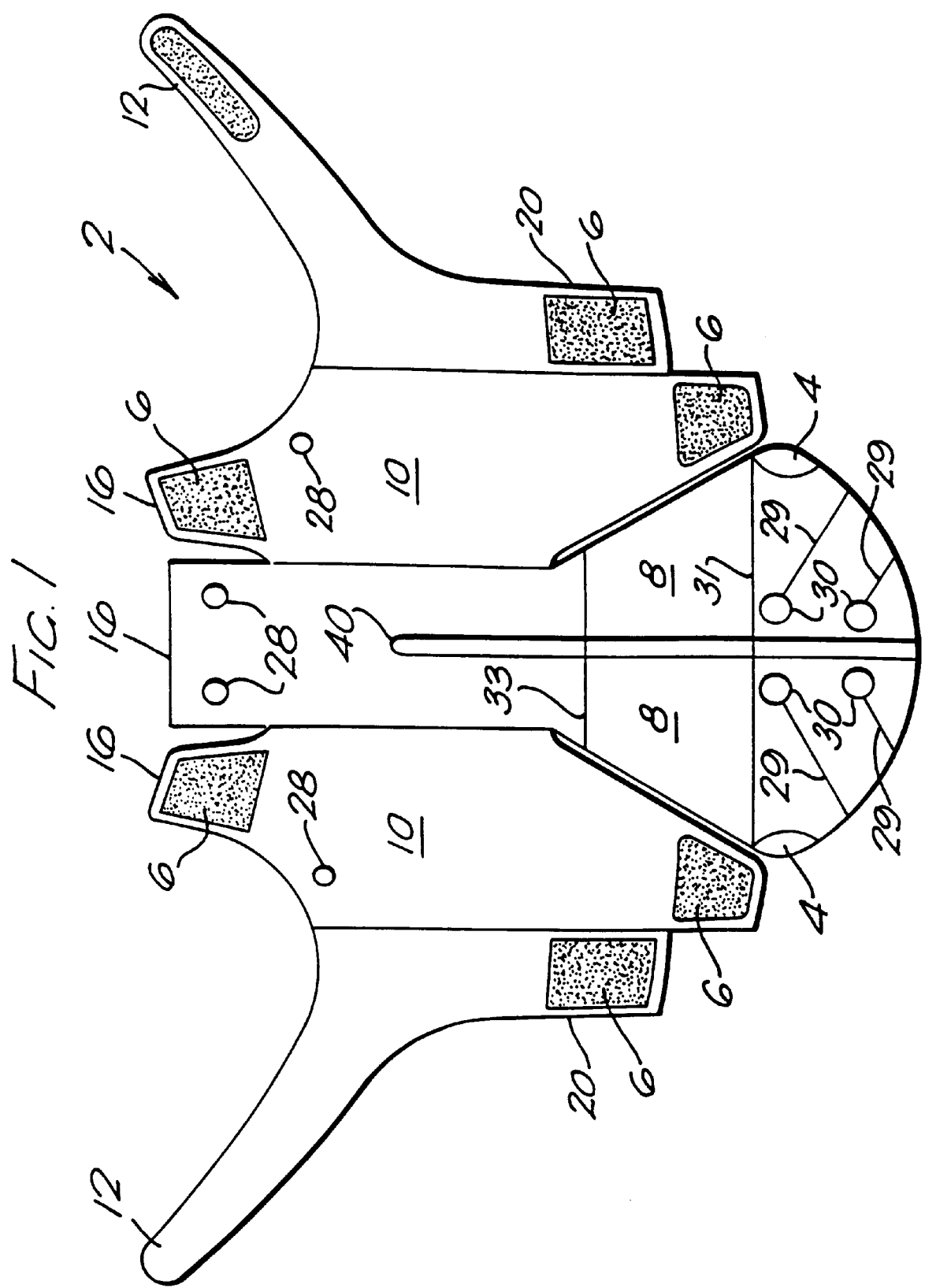

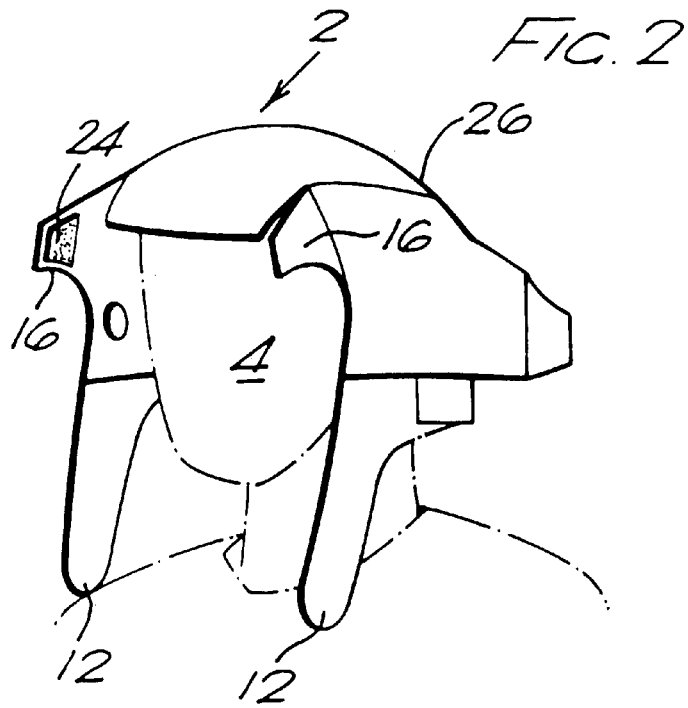
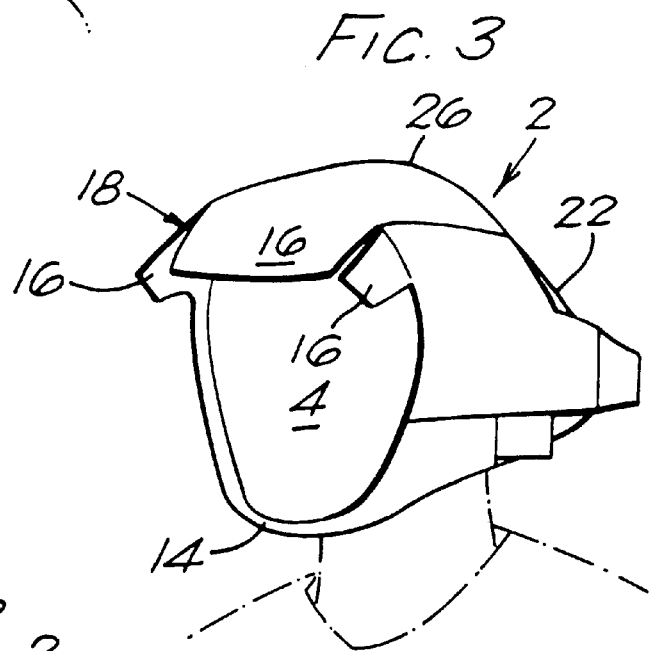
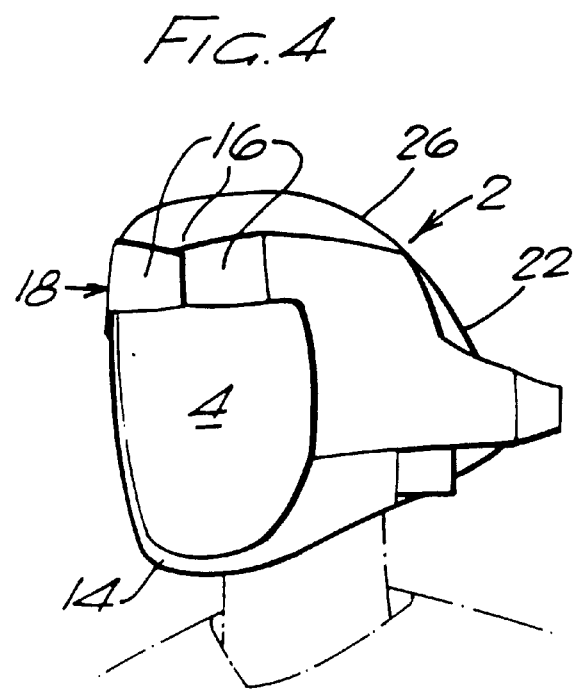

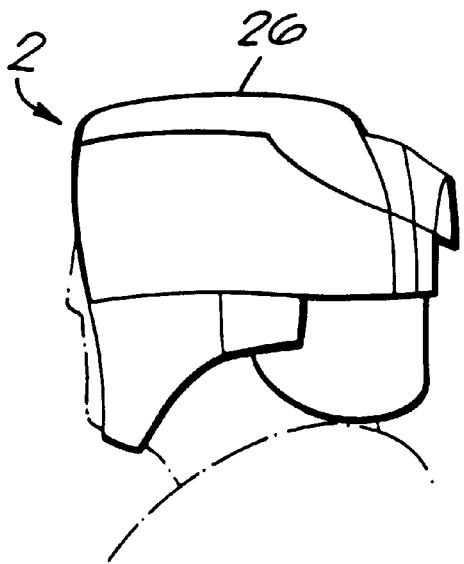
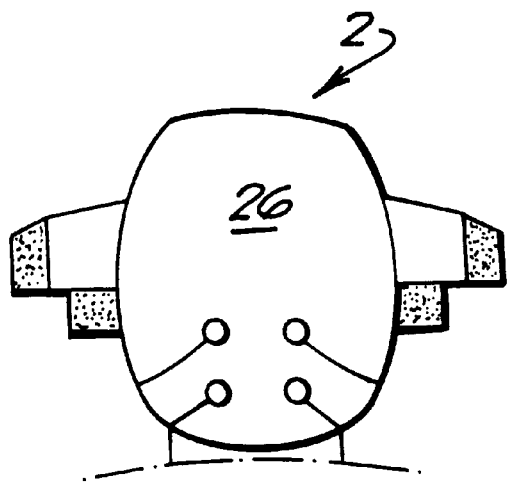
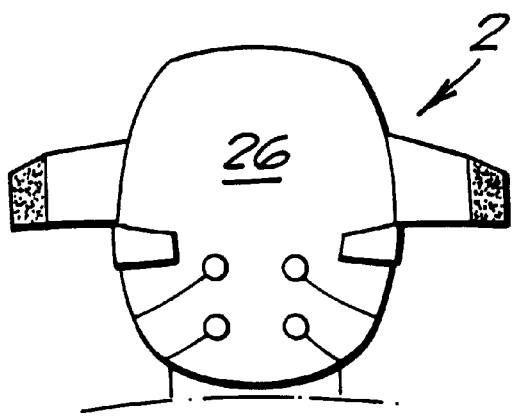
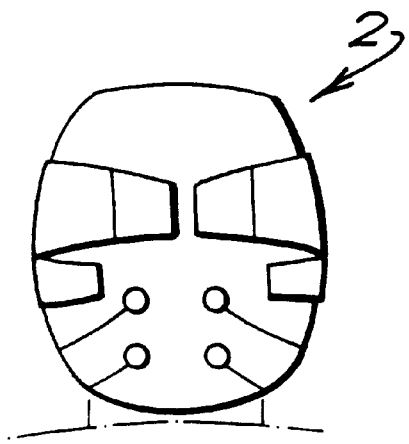

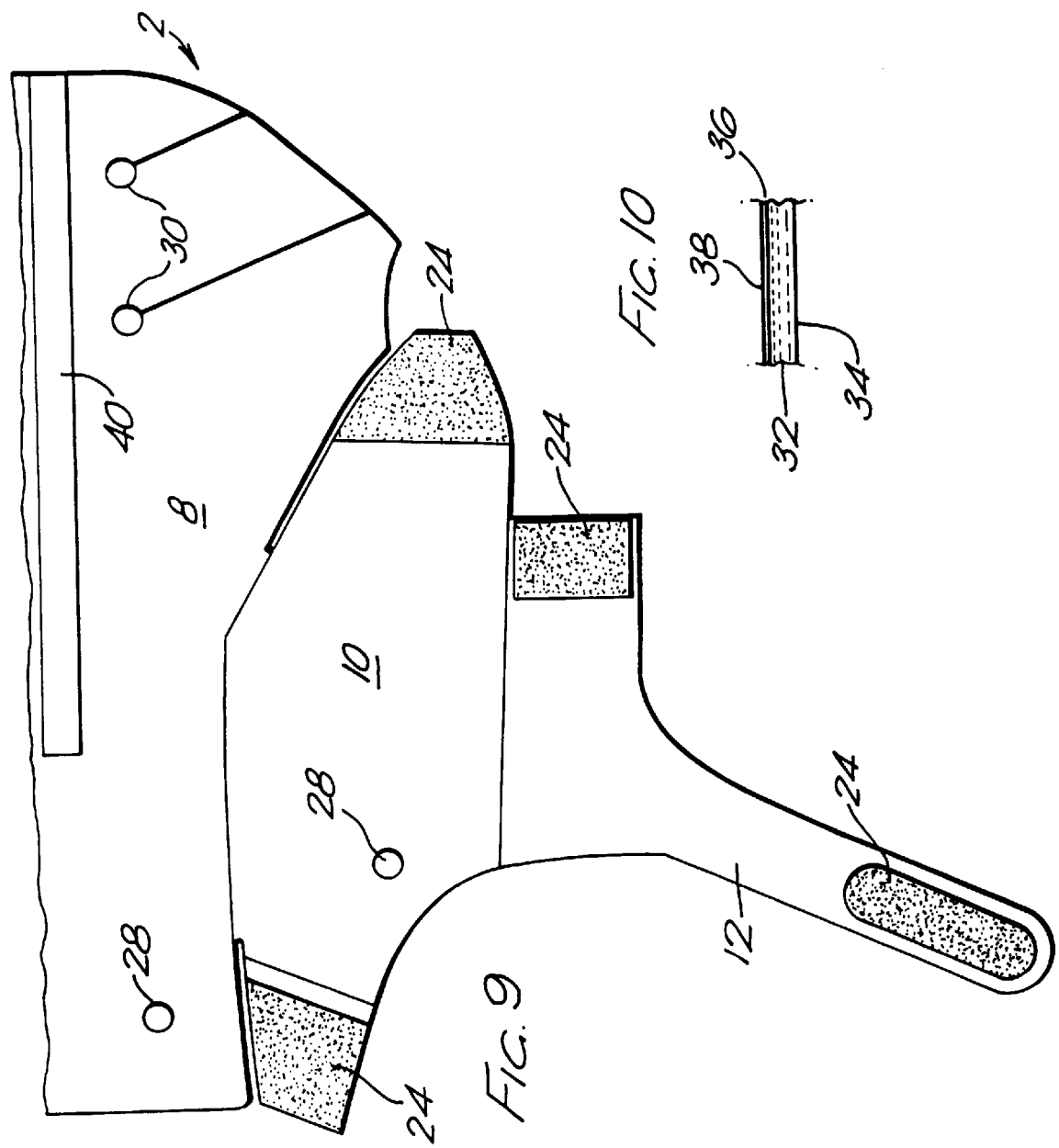

5,897,581

HEADWEAR FOR USE IN APPLYING COLD TO A PERSON'S SCALP

This invention relates to headwear for use in applying cold to a person's scalp.

It is medically known that cooling of the scalp is extremely effective in preventing hair loss induced by drugs given during chemotherapy treatment to cancer patients. The drugs given during chemotherapy are usually cytotoxic drugs. The cooling of the scalp constricts the blood supply to hair follicles in the scalp, thereby diminishing or preventing the hair follicles receiving high cytotoxic drug concentrations during the initial phases of chemotherapy. Furthermore, the coldness itself reduces the metabolism of cells of the hair follicles and thus reduces the ability of the cytotoxic drugs to act on the hair follicles. The combined effect of constricting the blood supply to the hair follicles and reducing the metabolism of the cells of the hair follicles prevents or reduces the hair loss.

It is known to cool the scalp by applying cooled gel packs or ice packs. The application of such packs is tedious and an even cooling of the scalp is not able to be achieved. An improved known method of cooling the scalp is to use an article of headwear like a helmet which contains between inner and outer skins a cold retaining medium such as a gel. The known helmets are not satisfactory in that they are not able to fit sufficiently snuggly on the heads of different persons, which heads may be of different sizes and shapes, and which heads may have different amounts of hair and hairstyles. This is an important disadvantage because the helmets are designed for re-use, for example in hospitals and similar establishments, and a wide variety of patients may need to wear the helmets.

It is an aim of the present invention to obviate or reduce the above mentioned problems.

Accordingly, the present invention provides headwear for use in applying cold to a person's scalp, which headwear is flat when it is not being worn, is foldable around a person's head when it is being worn, and is securable on the person's head by a plurality of fastener means, the headwear being such that the folding nature of the headwear and the plurality of fastener means enables the headwear to be folded as a close fit on the person's head irrespective of different persons with different shapes and sizes of head, and the headwear being such that it has double skinned portions which contain a cold retaining medium which gives up its cold to the person's scalp when the headwear is being worn, a chin strap, and a layer of insulating material for helping to prevent loss of cold from the headwear to the atmosphere.

The headwear of the present invention is advantageous in that it is able to be snuggly fitted on different sizes and shapes of head, with different amounts of hair and different types of hairstyles. The headwear can be snuggly fitted to give a tight compressive fit. The headwear is such that all parts of the head can be covered and the cold can be evenly distributed. Still further, the headwear can retain the cold better than many known types of headwear so that less numbers of cooled articles of headwear need to be worn by a patient during a period of treatment than has hitherto been necessary with many known types of headwear. A further advantage of the headwear of the present invention is that it is portable so that a patient is able to walk about, for example in order to go to the toilet or to relieve boredom, and the patient is not permanently connected to a mechanical air cooling machine. The headwear of the present invention can be produced to be of a light weight for so that it is not unduly uncomfortable to wear. Thus, for example, the headwear may be produced to weigh from 2 lbs 14 oz to 3 lbs 8 oz (1304.1–1587.6 gms)

The headwear may have a pair of straps which connect together to form the chin strap part of the headwear.

The headwear may have front flaps which connect together to form a part of the headwear for covering the front of the scalp and the temples. Preferably, there are three of the front flaps.

The headwear may have rear flaps which connect together to form a part of the headwear covering the ears, the back of the head and the neck. Preferably, there are five of the rear flaps.

Preferably, the fastener means are of a type having a plurality of interlocking plastics members. One type of such fastener means having a plurality of interlocking plastics members is sold under the registered trade mark Velcro.

The fastener means may comprise a plurality of pads of the plastics members and an outer surface to the headwear which is such that the pads can fasten to the outer surface, the pads being positioned at edge portions of the headwear when it is flat, and the headwear being such that the pads can be placed where appropriate on the outer surface of the headwear to form the headwear into the required shape for fitting closely on the person's head. When the above mentioned straps and flaps are employed, then the pads will usually be positioned on the straps and the flaps.

The outer surface of the headwear is preferably a raised looped brushed nylon material. A presently preferred material is 125 gms per square meter in weight and it is provided with a coat of polyurethane on its side remote from the raised looped brushed nylon type of material.

The headwear may be such that the double skinned portions form a top compartment for the cold retaining medium and two side compartments for the cold retaining medium.

The cold retaining medium is preferably a gel. A presently preferred gel is a glycol gel containing appropriate additives. Thus, for example, the glycol gel may be a pharmaceutical grade polypropylene glycol gel containing hydroxypropyl methylcellulose, titanium dioxide and water. The water may be added in a very hot but not boiling state to the polypropylene glycol and its additives. Alternatively, the water may be added in a cold state.

The cold retaining medium will usually be sealed inside the headwear, for example in the above mentioned top and two side compartments. Where the cold retaining medium is sealed in the headwear, then appropriate seals may be effected by radio frequency sealing. Other methods of sealing however may be employed.

Generally, the cold retaining medium will be chosen so that it has an operating temperature range of minus 25° C.–0° C. Also, the cold retaining medium will normally be chosen such that it is able to release its cold at a steady rate. By way of example, it is mentioned that where several caps will need to be worn by a patient for a treatment period, then the first cap may be designed to be able to be worn for three quarters of an hour, and subsequent caps may be designed to be worn for one hour each. Such prolonged cold release requires the cold retaining medium, for example the gel, to be correctly formulated. For example, if a gel is employed and it is too thin, then the gel heats up too quickly and the headwear does not give the required amount of cold for the required period. Conversely, if the gel is too thick it tends to freeze and thus the cap in its flat condition cannot easily be folded to form a snug fit on the person's head.

The headwear may be one in which the double skinned portions are made of a flexible sheet plastics material which is such that it retains its flexibility when the headwear is cooled for use on the person's head. A presently preferred flexible sheet plastics material is polyurethane. Other flexible sheet plastics materials may be employed but care must be taken to ensure that the plastics materials do not tend to crack when the headwear is cooled to minus 25° C. For example, polyvinyl chloride is not really suitable since it tends to crack at minus 15° C. Where polyurethane is employed, then the polyurethane flexible sheet plastics material is preferably 10 gauge.

The headwear may include weld points for use in thinning the cold retaining medium at desired parts of the headwear. The weld points may be so positioned as to thin the cold retaining medium over parts of the headwear adjacent the person's forehead and temples. At the weld points, the inner and outer skins of the double skinned portions are connected together.

The headwear may include seams for use in causing the cold retaining medium evenly to be distributed over the headwear. The seams will usually be welded seams which connect together the inner and outer skins of the double skinned portions. The inner ends of the seams may be provided with reinforcing weld points to reinforce the inner ends of the seams. Preferably, there are four of the seams but more or less than four of the seams may he employed if desired.

The headwear may include a layer of insulating material for helping to prevent loss of cold from the headwear to the atmosphere. The insulating material is preferably a foam insulating material or a felt insulating material. Any suitable and appropriate foam material may be employed. The layer of foam material may be one 0.0625 inch (0.1588 cm) thick. The insulating material helps to keep the cold in the cap and helps to stop the cold retaining medium from being heated by the environment to ambient temperature.

The headwear may include holder means for a temperature monitor. The holder means may be a pocket. If desired, the holder means may be provided in a head band arrangement which is separate from the headwear. If desired, more than one temperature monitor may be employed so that, for example, up to five temperature monitors may be employed.

The temperature monitor may be connected to a display device which is attached to a person's waist. Such a display device enables the temperatures monitored by the temperature monitor easily to be seen so that a close check can be carried out to ensure that the scalp does not rise above the temperature at which scalp cooling will become inefficient.

The temperature monitor and the display device may form part of control means for the headwear, for example for controlling how the headwear is used. Thus, for example, the control means may have various visual and/or audible warning systems to ensure that the headwear is initially worn for a correct period to bring the scalp to a desired temperature prior to starting chemotherapy treatment. Too long a period or too short a period would mean that the scalp was not at the correct temperature for the chemotherapy treatment. Also, the control means can be used to indicate an allowed time period for changing the headwear when the headwear has given up its cold and needs to be replaced by fresh headwear. Further, the control means may indicate the time remaining on a treatment period. Advantageously, the control means is able to store information as to how the headwear has been used, and to be connected to a printer to obtain a hard copy printout of the stored information. Also advantageously, only parts of the stored information are printed, these parts being selected parts relevant to the use of the headwear, for example to show when the headwear has not been used properly. This avoids generating large printouts.

The headwear of the present invention may be made in different colours to indicate headwear which will cool to different temperatures and/or which will last for different periods of time. The different colours may also be used by, for example, nursing staff and doctors, as a means of indicating whether the headwear is the patient's first, second or third etc. article of headwear in any particular course of treatment.

Embodiments of the invention will now be described solely by way of example and with reference to the accompanying drawings in which:

FIG. 1 is a view from below of first headwear folded flat;

FIGS. 2–8 show different views from the front to the back and illustrate how the headwear in the flat form shown in FIG. 1 is folded around a person's head;

FIG. 9 is an enlarged view of half of the flat headwear shown in FIG. 1 and illustrates in more detail the construction of the headwear;

FIG. 10 is a section through part of the headwear;

Figure 11:
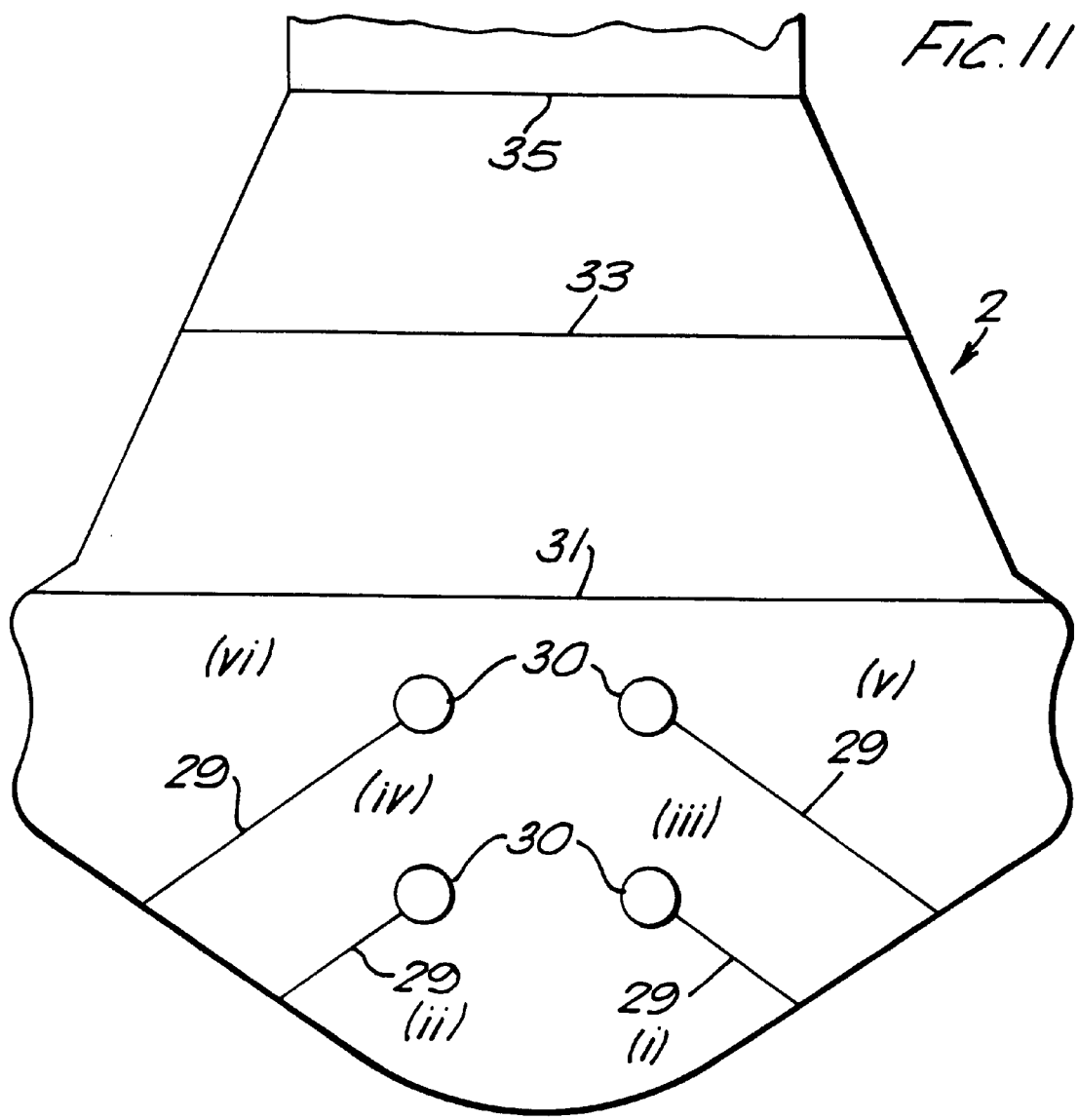
FIG. 11 is a plan view of part of second headwear folded flat.

Referring to FIGS. 1–10, there is shown headwear 2 for use in applying cold to a person's scalp. The headwear 2 is flat when it is not being worn, as shown in FIG. 1. The headwear 2 is foldable around a person's head 4 when it is being worn, the folding process being illustrated in FIGS. 2–8. The headwear 2 is also such that it is securable on the person's head 4 by a plurality of fastener means 6.

The headwear 2 is such that the folding nature of the headwear 2 and the plurality of fastener means 6 enables the headwear 2 to be folded as a close fit on the person's head 4 irrespective of different persons with different sizes and shapes of head. The headwear 2 is also such that it has double skinned portions 8, 10 which contain a cold retaining medium which gives up its cold to the person's scalp when the headwear 2 is being worn.

The headwear 2 comprises a pair of straps 12 which connect together to form a chinstrap part 14 of the headwear 2. The headwear 2 also has three front flaps 16 which connect together to form a part 18 of the headwear for covering the front of the scalp and the temples of the person's head 4.

The headwear 2 still further has five rear flaps 20 which connect together to form a part 22 of the headwear 2 for covering the ears, the back of the head and the neck of the person's head 4.

The fastener means 6 are of the type having a plurality of interlocking plastics members known as Velcro (Registered Trade Mark) These plastics members are in the form of pads 24 as shown most clearly in FIG. 9. The fastener means also comprises an outer surface 26 to the headwear 2, which outer surface is made of a brushed nylon type of material known as Vel-Luch (Registered Trade Mark). This outer surface is such that the pads 24 can be placed where appropriate on the outer surface 26 of the headwear 2 to form the headwear 2 into the required shape for fitting closely on the person's head 4. As can be seen from the drawings, the pads 24 are on the ends of the straps 12 and the flaps 16, 20.

The double skinned portions 8, 10 form a top compartment for the cold retaining medium and two side compartments for the cold retaining medium. The cold retaining medium is preferably a gel. The gel is preferably a polypropylene glycol gel with additives such as hydroxypropyl methylcellulose and titanium dioxide. The gel is sealed in the headwear 2 and the various necessary sealing lines are formed by radio frequency welding.

The double skinned portions are made of flexible sheet plastics material which is such that it retains its flexibility when the headwear 2 is cooled down to minus 25° C. This flexible material is 10 gauge polyurethane material.

As can be seen from FIGS. 1 and 9, the headwear 2 includes weld points 28 for use in thinning the cold retaining medium at desired parts of the headwear 2. More specifically, these weld points 28 are so positioned as to thin the cold retaining medium over parts of the headwear 2 adjacent the person's forehead and temples.

The headwear 2 contains four seams 29 which terminate at their inner ends in reinforcing weld points 30. The seams 29 form interconnecting pockets and they cause the cold retaining medium evenly to be distributed over the headwear 2. The seams 29 help to prevent the cold retaining medium from sagging when the headwear 2 is being worn. The weld points 28, 30 and the seams 29 are preferably formed by radio frequency welding.

The headwear 2 also has seams 31 and 33 which are employed to help to maintain the cold retaining medium in place and evenly distributed whilst the headwear 2 is being worn.

FIG. 10 shows the cold retaining medium in the form of a gel 32 positioned between inner and outer skins 34, 36 respectively of the double skinned portions 8, 10. The inner and outer skins 34, 36 can be 10 gauge sheet polyurethane. The outer skin 36 is then laminated to an outer skin 38 which has the brushed nylon outer surface 26.

As shown in FIGS. 1 and 9, the headwear 2 is provided with holder means in the form of a long pocket 40. The pocket 40 is for receiving a temperature monitor for monitoring the temperature of the scalp of the person's head 4. The temperature monitor (not shown) may be connected to a display device (not shown) which may be attached to any suitable part of the person and is preferably attached to the person's waist. The temperature monitor and the display device form part of control means for controlling the use of the headwear 2.

In order that the invention will be fully understood, reference will now be made to the following example.

EXAMPLE

The gel 32 shown was formulated as a 100 gallon mixture (454.6 l) from the following ingredients:

1. Fifty gallons (227.3 l) of polypropylene glycol (pharmaceutical grade).
2. Seventeen pounds (7711.2 gms) of hydroxypropyl methyl-cellulose.
3. Seven pounds (3175.2 gms) of titanium dioxide.
4. Fifty gallons (227.3 l) of very hot but not boiling water.

The polypropylene glycol, the hydroxypropyl methylcellulose and the titanium dioxide were mixed together. The water was then added. All the four ingredients were then continuously thoroughly mixed for 90 minutes.

The polypropylene glycol is employed to enable the gel to remain soft at minus 20° C. The titanium dioxide is used for whitening the gel to give it a cosmetic look. The hydroxypropyl methylcellulose is a gelling agent which enables the formulated gel to store cold energy.

The headwear 2 can be satisfactorily used to reduce scalp temperatures down from 31° C. to approximately plus 7° C. in a short space of time. The quick cooling of the scalp temperature is advantageous in that the blood vessels feeding the hair follicles in the scalp quickly constrict and this helps to prevent the cytotoxic alopecia-inducing drugs reaching the hair follicles. The scalp temperature will start to rise as the headwear 2 begins to run out of cold energy. The headwear 2 can then be removed and can be replaced by a new cold article of headwear 2.

It is preferred that the scalp temperature should not rise above 17° C. as otherwise the blood vessels in the scalp tend to dilate and then allow the cytotoxic drugs to the hair follicles, with resultant hair loss.

Generally, the first article of headwear used may be used for half an hour or three quarters of an hour. This article of headwear may then be removed and replaced by a fresh cold article of headwear. The second article of headwear may reduce scalp temperatures down to 0° C. and may be effective to maintain the scalp temperature below plus 17° C. for at least three quarters of an hour. The length of time that scalp cooling should be administered is dependent upon the various drugs that are used for the chemotherapy and the half life of those drugs.

The above mentioned display device for reading the scalp temperature can be easily secured to the patient's waist using straps or ties, and can easily be checked by medical staff at appropriate intervals. If desired, the control means may be arranged to give an audible warning when the scalp temperature approaches 15° C. after the temperature has been reduced below this figure.

The control means may also include an in-built timer which can be preset from half an hour to several hours as a safety backup to a technical fault developing which would stop the temperature monitor giving its audible warning when it senses scalp temperatures approaching 15° C. In order to ensure that the headwear 2 is portable, the control means can advantageously be arranged to run on one or more small batteries. The control means may be of any suitable and appropriate design so that, for example, it may have a stiffened wire probe.

It will be appreciated that the initial shape of the headwear 2 as shown in FIG. 1 is very important. This shape enables the headwear 2 to be folded around the person's head 4 as shown in FIGS. 2–8 and to fit equally firmly on small heads and large heads. This is especially important when it is borne in mind that the headwear 2 will be repeatedly used for patients having different shapes and sizes of heads. The correct degree of compression is important for transferring cold into the scalp.

Where the headwear 2 has felt or foam insulation, A section of the felt or foam insulation may be removed to give extra cold energy at appropriate points at the back of the head. This is because at the back of the head there are branches of occipital arteries which cause hotspots during cooling. The temperature of the blood vessels feeding the hair follicles at these points tends to rise above 17° C. If this happens then damage is done to these hair follicles and thinning of the hair or total hair loss occurs at these points.

The headwear 2 may be cooled in air cooled cold storage units which are able accurately to cool lots of articles of the headwear 2, all to substantially the same temperature. The cold storage units may have shelves for receiving the articles of headwear 2. When an article of headwear 2 is removed from the cold storage unit, it should be placed in a plastics type freeze box with a lid and the whole box should be taken to the patient. The lid can then be removed and the headwear 2 can be placed on the patient's head. The use of the freeze box helps to retain the cold in the headwear 2 whilst it is being taken to a patient.

After use, the headwear 2 may be washed in soapy water and dried prior to re-use. When the caps are being cooled, the brushed nylon outer surface 26 should be positioned to the inside so that the inner skin 34 is exposed to the cold in the cold storage unit. This enables the gel to absorb the required cold energy as quickly as possible.

Figure 12:
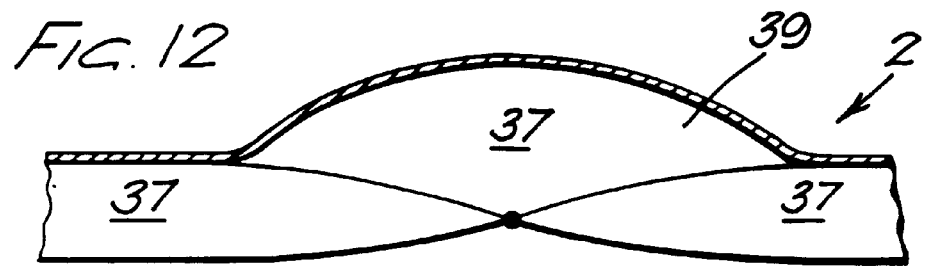
FIG. 12 is a section through part of the second headwear when it is flat.
Figure 13:
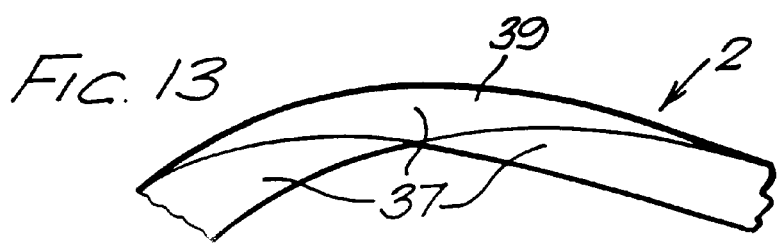
FIG. 13 is a section through part of the second headwear when it is on a person's head.

Referring now to FIGS. 11–13, there is shown part of second headwear 2 of the invention. Similar parts as in previous Figures have been given the same reference numerals.

FIG. 11 shows how the welded seams 29 and 31 form six inter-connected compartments (i)–(vi). These compartments help to keep the cold retaining medium evenly distributed over the headwear 2 when it is being worn and they help to stop the cold retaining medium sagging towards the person's neck and thus leaving parts of the headwear 2 with none, or an insufficient amount, of the cold retaining medium.

In FIG. 11, the headwear 2 is shown with a further welded seam 35.

FIG. 12 illustrates how the cold retaining medium 37 is formed in a pouch 39 between the weld seams 31, 35. This pouch is domed as can be seen from FIG. 12. However, when the headwear 2 is being worn as shown in FIG. 13, then it will be seen that the pouch 39 has decreased in size so that the gel 37 in the pouch 39 is substantially of the same thickness as the gel 37 outside the pouch 39.

It is to be appreciated that the embodiments of the invention described above with reference to the accompanying drawings have been given by way of example only and that modifications may be effected. Thus, for example, the precise shape of the headwear 2 may vary from that shown in the drawings. The pocket 40 may be omitted and, for example, up to five temperature monitors may be provided is a separate head band arrangement.

We claim:

1. Headwear for use in applying cold to a person's scalp, which headwear is flat when it is not being worn, is foldable around a person's head when it is being worn, and is securable on the person's head by a plurality of fastener means: the headwear being such that the folding nature of the headwear and the plurality of fastener means enables the headwear to be folded as a close fit on the person's head irrespective of different persons with different shapes and sizes of head; the headwear being such that it has double skinned portions which contain a cold retaining medium which gives up its cold to the person's scalp when the headwear is being worn, a chin strap, and a layer of insulating material for helping to prevent loss of cold from the headwear to the atmosphere; and the headwear being such that part of the headwear that covers the back of the head has an extra thickness of cold retaining medium which provides extra cold at the back of the head where there are branches of occipital arties which cause hot spots during cooling of the person's scalp, whereby even cooling all over the person's scalp is achieved.

2. Headwear according to claim 1 in which the fastener means comprises a plurality of pads of interlocking plastics members, and in which an outer surface of the headwear is such that the pads are fastenable to the outer surface, the pads being positioned at edge portions of the headwear when it is flat, and the headwear being such that the pads can be placed where appropriate on the outer surface of the headwear to form the headwear into the required shape for fitting closely on the person's head.

3. Headwear according to claim 2 in which the outer surface of the headwear is a raised looped brushed nylon material.

4. Headwear according to claim 1 in which the cold retaining medium is polypropylene glycol gel containing hydroxypropyl methylcellulose, titanium dioxide and water.

5. Headwear according to claim 1 and including weld points for use in thinning the cold retaining medium at desired parts of the headwear, the weld points being so positioned as to thin the cold retaining medium over parts of the headwear adjacent the person's forehead and temples, and the headwear including seams for use in causing the cold retaining medium evenly to be distributed over the headwear.

6. Headwear according to claim 1 in which the insulating material is a foam insulating material or a felt insulating material.

7. Headwear according to claim 1 and including holder means for a temperature monitor.

8. Headwear according to claim 7 in which the holder means is a pocket.

9. Headwear for use in applying cold to a person's scalp, which headwear is flat when it is not being worn, is foldable around a person's head when it is being worn, and is securable on the person's head by a plurality of fastener means: the headwear being such that the folding nature of the headwear and the plurality of fastener means enables the headwear to be folded as a close fit on the person's head irrespective of different persons with different shapes and sizes of head; the headwear being such that it has double skinned portions which contain a cold retaining medium which gives up its cold to the person's scalp when the headwear is being worn, a chin strap, and a layer of insulating material for helping to prevent loss of cold from the headwear to the atmosphere; the headwear being such that the double skinned portions are made of a flexible sheet polyurethane plastics material; and the headwear being such that it comprises front flaps which connect together to form a part of the headwear for covering the front of the scalp and the temples, and rear flaps which connect together to form a part of the headwear covering the ears, the back of the head and the neck, the rear flaps being such as to include a centrally positioned rear flap which is pear-shaped when the headwear is flat.

* * * * *